United States Patent
Win et al.

(10) Patent No.: US 8,317,721 B2
(45) Date of Patent: Nov. 27, 2012

(54) REUSEABLE SKIN TESTING DEVICE

(76) Inventors: Patrick Win, St. Louis, MO (US);
Edwin A. Reed, Pleasant Hill, MO (US)

( * ) Notice: Subject to any disclaimer, the term of this patent is extended or adjusted under 35 U.S.C. 154(b) by 230 days.

(21) Appl. No.: 12/925,142

(22) Filed: Oct. 14, 2010

(65) Prior Publication Data
US 2011/0118624 A1    May 19, 2011

Related U.S. Application Data

(60) Provisional application No. 61/278,935, filed on Oct. 15, 2009.

(51) Int. Cl.
*A61B 5/00* (2006.01)
(52) U.S. Cl. ........................................ 600/556
(58) Field of Classification Search .................. 600/556
See application file for complete search history.

(56) References Cited

U.S. PATENT DOCUMENTS

| | | | |
|---|---|---|---|
| 2,522,309 A | 9/1950 | Simon | |
| 4,711,247 A | 12/1987 | Fishman | |
| 5,097,810 A | 3/1992 | Fishman | |
| 5,551,441 A | 9/1996 | Pitesky | |
| 5,647,371 A | 7/1997 | White | |
| 5,671,753 A * | 9/1997 | Pitesky | 600/556 |
| 5,673,705 A * | 10/1997 | Pitesky | 600/556 |
| 5,692,518 A | 12/1997 | Baker | |
| 5,944,671 A | 8/1999 | White | |
| 6,024,706 A * | 2/2000 | Hsiao | 600/556 |
| 6,095,988 A | 8/2000 | Doll | |
| 6,206,838 B1 | 3/2001 | Doll | |
| 6,322,520 B1 * | 11/2001 | Baik | 600/556 |
| 6,419,414 B1 * | 7/2002 | Broyles et al. | 401/132 |
| 6,622,730 B2 * | 9/2003 | Ekvall et al. | 128/898 |
| 7,031,432 B2 * | 4/2006 | Geitz | 378/65 |
| 8,172,868 B2 * | 5/2012 | Eastman | 606/186 |
| 2002/0016527 A1 * | 2/2002 | Hancock | 600/213 |
| 2003/0149331 A1 * | 8/2003 | Geitz | 600/4 |
| 2004/0030237 A1 * | 2/2004 | Lee et al. | 600/414 |
| 2004/0210122 A1 * | 10/2004 | Sieburg | 600/393 |
| 2004/0230099 A1 * | 11/2004 | Taylor et al. | 600/204 |
| 2004/0230101 A1 * | 11/2004 | Martin et al. | 600/210 |
| 2005/0197596 A1 * | 9/2005 | Bellucci et al. | 600/573 |
| 2006/0167375 A1 * | 7/2006 | Terrassse et al. | 600/556 |
| 2006/0173469 A1 * | 8/2006 | Klein et al. | 606/144 |
| 2007/0043359 A1 * | 2/2007 | Altarac et al. | 606/61 |
| 2007/0055108 A1 * | 3/2007 | Taylor et al. | 600/210 |
| 2008/0046008 A1 * | 2/2008 | Smith et al. | 606/220 |
| 2008/0097441 A1 * | 4/2008 | Hayes et al. | 606/64 |
| 2009/0118662 A1 * | 5/2009 | Schnall | 604/20 |
| 2010/0100005 A1 * | 4/2010 | Mir et al. | 600/556 |
| 2010/0152810 A1 * | 6/2010 | Minogue et al. | 607/48 |

* cited by examiner

*Primary Examiner* — Sean P Dougherty
*Assistant Examiner* — Michael C Stout
(74) *Attorney, Agent, or Firm* — Charles McCloskey

(57) ABSTRACT

The present invention provides a device and method for skin testing. The device includes a handle assembly connected to a cylinder assembly having a first and second cylinder housing. Each cylinder housing is connected to at least one testing head assembly that includes a plurality of pins having a plurality of tips positionable against the skin and a socket assembly that is structured and operable to pivot the testing head to apply equal and even pressure to all the pins. Further, the method provides positioning the device tangent to the surface of the skin, and pivoting the testing head assembly horizontally to apply equal and even pressure to the pins.

9 Claims, 10 Drawing Sheets

REUSEABLE SKIN TESTING DEVICE

CLAIM OF PRIORITY

This patent application claims the benefit of priority, under 35 U.S.C. Section 119(e), to Patrick Win and Edwin Reed, U.S. Provisional Patent Application Ser. No. 61/278,935, entitled "SockeTest," filed on Oct. 15, 2009.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the data as described below and in the drawings that form a part of this document: Copyright 2010, WinReed Medical Technologies, LLC. All Rights Reserved.

TECHNICAL FIELD

This invention pertains generally to devices for use in testing for allergies, and more particularly, but not by way of limitation, to a reuseable skin-testing device.

BACKGROUND OF THE INVENTION

An estimated 50 million Americans suffer from one or more types of allergies, for example seasonal (e.g., perennial) allergies to hay fever; pet allergies to cat or dog dander or bee stings; indoor allergies to dust mites or cockroach allergen; outdoor allergies to mold spores or grass, trees or weed pollen; skin allergies to plants such as poison ivy, oak, and sumac or to materials such as latex; foods allergies to milk, soy, eggs, wheat, shellfish, treenuts, peanuts, fish; allergies to medicine such as penicillin. All ages, sex and racial groups are susceptible to allergies. A person may be tested to determine how he may react to specific allergens. Skin testing is one type of test that is utilized to determine what allergens may cause an allergic reaction to the patient. Skin testing may involve pricking, puncturing, or scratching the skin with an allergen. In addition, the skin may be tested with histamine or salt water to provide the physician with a control. A positive skin test may show a raised bump (e.g., called a wheal) that may be surrounded with redness (e.g., called the flare). The size of the bump determines whether the patient is allergic to a particular allergen. Typically the patient may be subjected to ten to seventy different allergens. This requires the use of a multi-headed skin-testing device.

Current multi-headed skin testing devices are utilized when skin testing for allergies. One issue with such multi-headed skin testing devices is the occurrence of false positive results. False positive results occur because of an uneven and equal pressure applied to contact points (e.g., tips) with a multi-headed device. For example, some tips have more pressure applied than other tips, resulting in the false positive. Thus, there is a need for an equal and even amount of pressure to be applied to all the tips of a multi-headed skin-testing device to eliminate false positive results.

SUMMARY OF INVENTION

The present invention provides a device and method for skin testing. The device includes a handle assembly connected to a cylinder assembly having a cylinder first and second cylinder housing. The cylinder housing is connected to at least testing head assembly. The testing head assembly includes a plurality of pins positionable against the skin and a socket assembly structured and operable to pivot the testing head assembly to apply equal and even pressure to all the pins.

Further, the method provides for testing patients to an allergen. The method includes positioning a skin-testing device on the surface of the skin. The device having a handle assembly connected to a cylinder assembly, the cylinder assembly structured and operable to attach to a plurality of testing head assemblies. The testing head assemblies include a plurality of pins structured to be coated with an allergen. The pins structured and operable to prick the surface of the skin. The testing head assemblies further include a release mechanism structured and operable to pivot the testing head assembly. The method further including a step of pivoting the testing head assembly horizontally to apply equal and even pressure to the pins.

BRIEF DESCRIPTION OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, various embodiments discussed in the present invention.

DETAILED DESCRIPTION OF THE INVENTION

Figure 1:
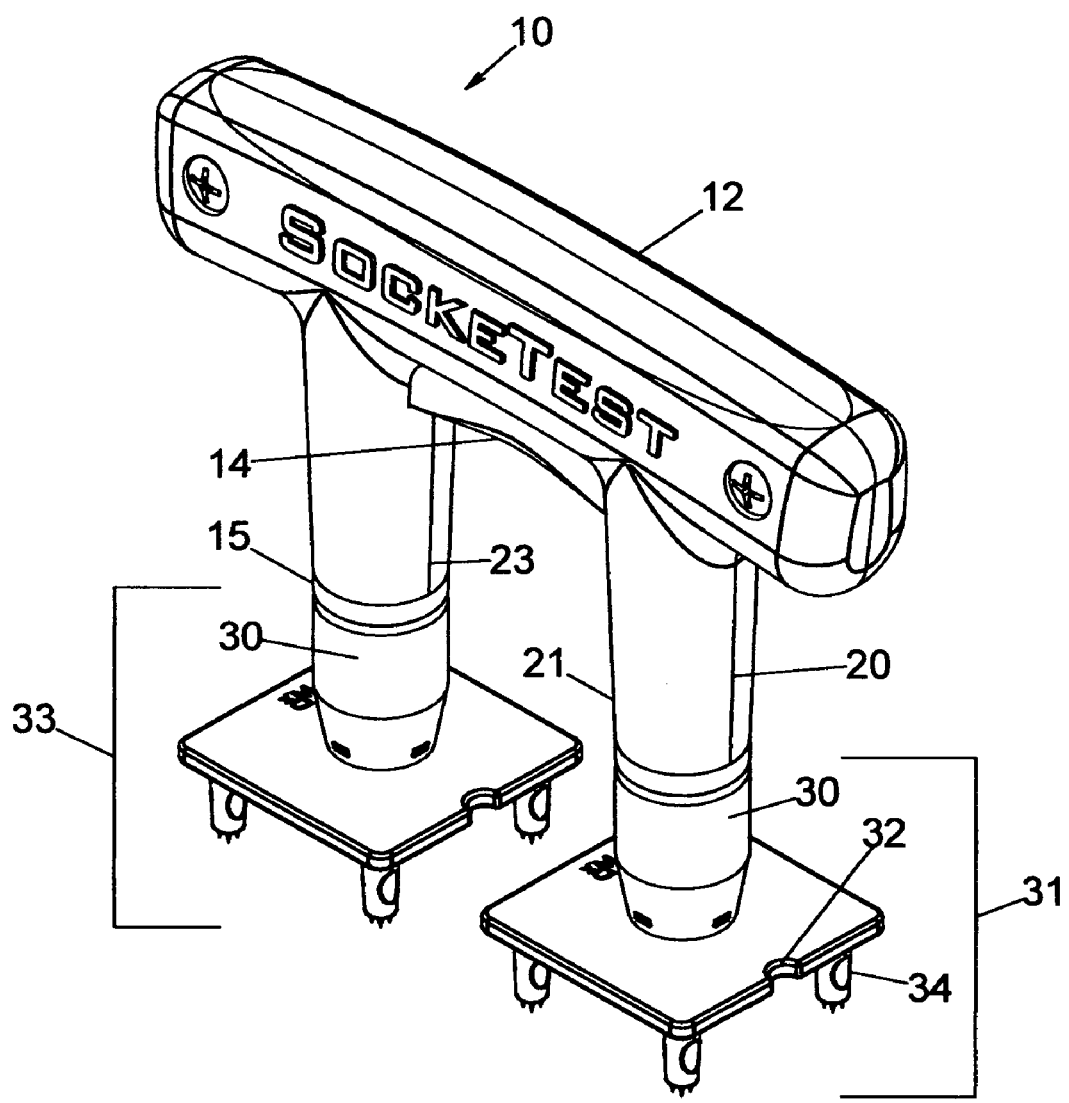
FIG. 1 shows a skin-testing device.

FIG. 1 shows a skin-testing device 10 used by a health care worker (e.g., nurse, physician and the like) to test a patient (e.g., human or animal) for sensitivities to certain allergens, (e.g., allergies). The skin-testing device 10 includes a handle 12, a trigger mechanism 14, a collar 15 located between a cylinder assembly 20, and a testing head assembly 30. The handle 12 may be manufactured by injection molding using an impact resistant Acrylonitrile Butadiene Styrene ("ABS") plastic, or other plastic material that provides lightweight and durability.

In one embodiment, the skin testing device 10 has the handle 12 connected the cylinder assembly 20. Cylinder assembly 20 includes a first cylinder housing 21 and a second cylinder housing 23. The first cylinder housing 21 and the second cylinder housing 23 are separated by a predetermined distance. Each cylinder housing 21, 23 are operatively connected to one of two testing head assembly 30. In one embodiment, cylinder housings 21, 23 are operatively connected to at least two testing head assemblies 30. The testing head assembly 30 includes a plurality of pins 34, where each pin has a plurality of tips (shown in FIG. 4C).

Other embodiments of the skin-testing device 10 may be used. For instance, an embodiment may include more than two cylinder assemblies 20 and more than two testing head assemblies 30. For example, the skin testing device 10 may include two handles 12 structurally arranged in an x-type pattern, with a cylinder housing 20 structurally connected to each of the four ends of the X. A pair of testing head assemblies 30 are structurally and operably connected to the end of each of the four cylinder housings 20. (Not shown).

Figure 2A:
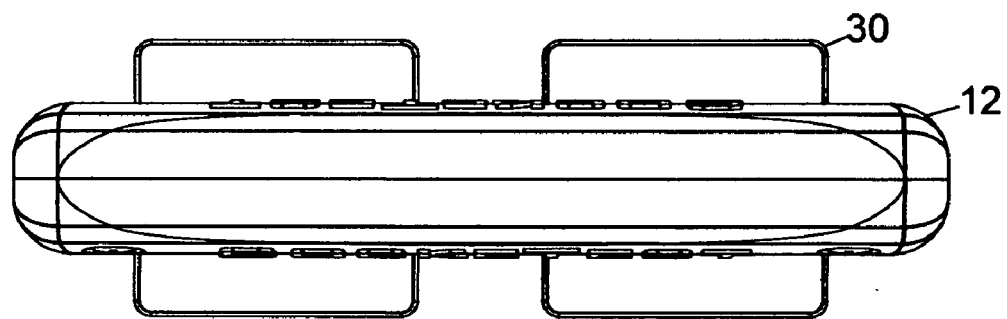
FIG. 2A shows a top view of the skin-testing device shown in FIG. 1.
Figure 2B:
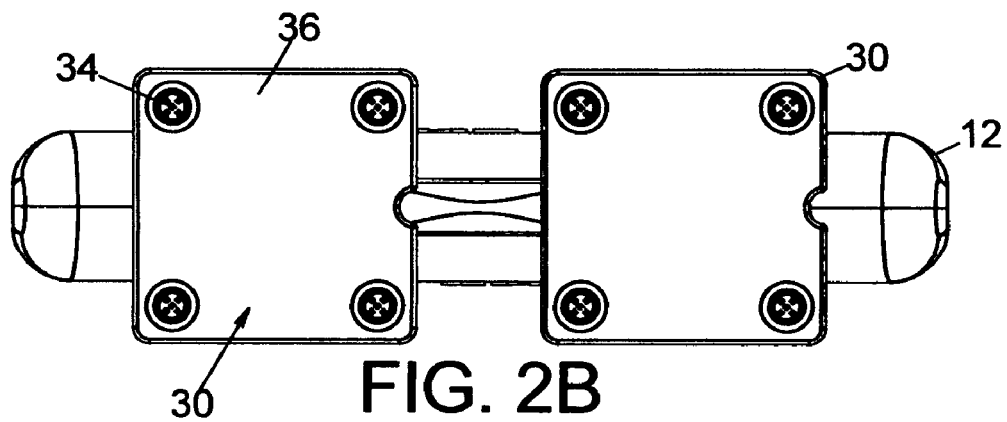
FIG. 2B shows a bottom view of the skin-testing device shown in FIG. 1.

FIG. 2A shows a top view of the skin-testing device 10. FIG. 2B shows a bottom of the skin testing device 10 having at least two testing head assemblies 30 connected to the device 10, where each testing head assembly 30 has four pins 34. In one embodiment the four pins 34 are arranged at the four corners of a baseplate 35. In other embodiments, more than four pins 34 may be utilized in various configurations. For instance, pins 34 may be located at each corner of the baseplate 35, and one pin 34 may be located in the center of the baseplate 35 (e.g., five pins). Or, there may be multiple rows of pins. For instance, two rows of pins 34 may be utilized, where each row is separated a predetermined distance from an adjacent row; and each row has at least three pins 34 (e.g., six pins). Alternatively, three rows of pins 34 may be utilized, where each row is separated a predetermined distance from an adjacent row; and each row has at least three pins 34 (e.g., nine pins).

Figure 3A:
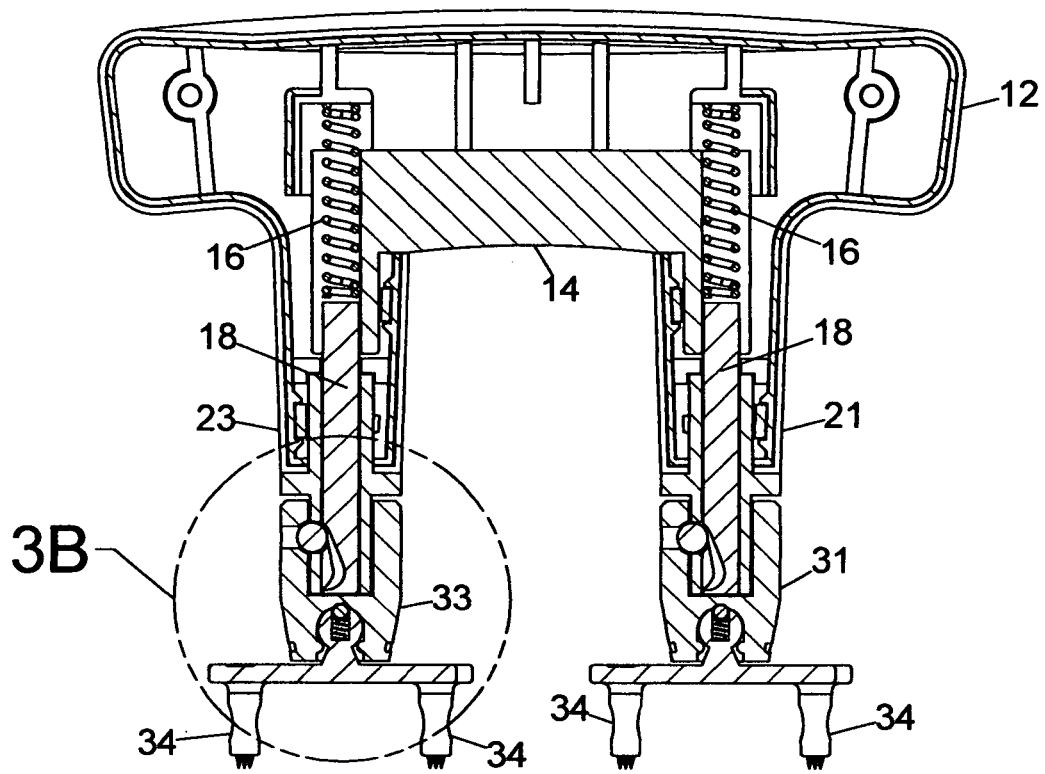
FIG. 3A shows a cross-section of the skin-testing device shown in FIG. 1.
Figure 3B:
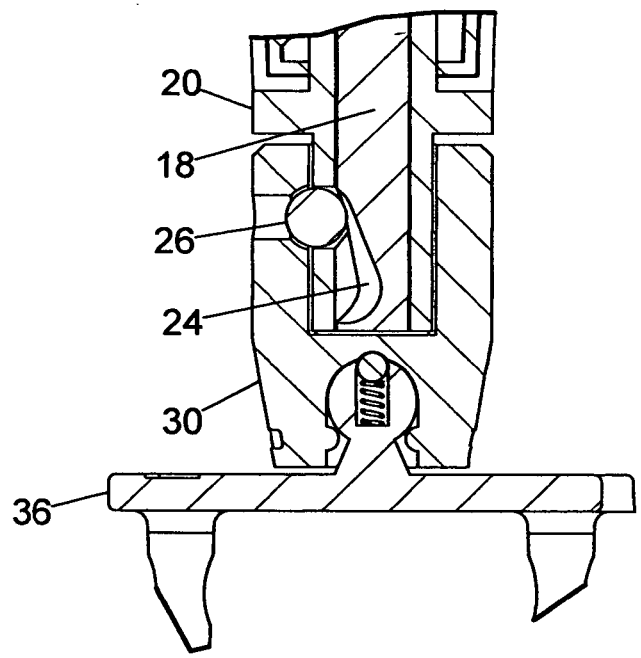
FIG. 3B show an enlarged view of a cylinder housing connected to a testing head assembly shown in FIG. 3A.

FIG. 3A shows a cross-section of the skin testing device 10 shown in FIG. 1, and FIG. 3B shows an enlarged view of a cylinder housing connected to a testing head assembly shown in FIG. 3A. The handle 12 is connected to they cylinder assembly 20, the cylinder assembly 20 having a first cylinder housing 21 and a second cylinder housing 23. The first cylinder housing 21 is removeably connected to a testing head assembly 31, and the second cylinder housing is removeably connected to a testing head assembly 33. Cylinder housing 21, 23 include a cylinder bearing shaft 18 having a pocket 24. The cylinder bearing shaft 18 may be manufactured from high-grade stainless keel. The pocket 24 is structured to receive a bearing 26 (e.g., a 4 mm ball bearing and the like). The handle 12 further includes a trigger mechanism 14 having a biasing device 16 (e.g., a spring, a pneumatic cylinder, a rubber band and the like), where the biasing device 16 is connected to the cylinder bearing shaft 18. The biasing device 16 maybe manufactured from a high-grade stainless steel, a corrosion resistant grade of steel, and manufactured so that the biasing device 16 has the kinematic properties of a compression spring. Trigger mechanism 14 is structured and operable to compress the biasing device 16 such that the cylinder bearing shaft 18 receives the bearing 26 in the pocket 24.

In one embodiment, the testing head assembly 30 may be removed and replaced. For example, the testing head assembly 30 may be disconnected from the cylinder housing 21 when the trigger mechanism 14 is compressed. Compressing trigger mechanism 14 causes the biasing device 16 to be compressed. The compressed biasing device 16 moves the cylinder bearing shaft 18 longitudinally along a vertical axis of the cylinder housing 21, thereby resulting in the bearing 26 to move into pocket 24.

Figure 4A:
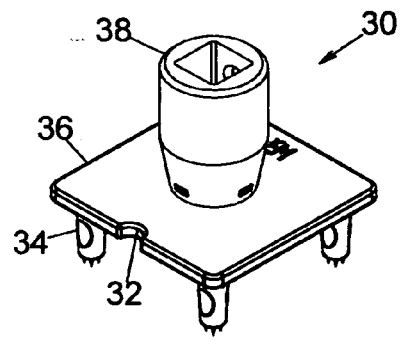
FIG. 4A show a testing head assembly.
Figure 4B:
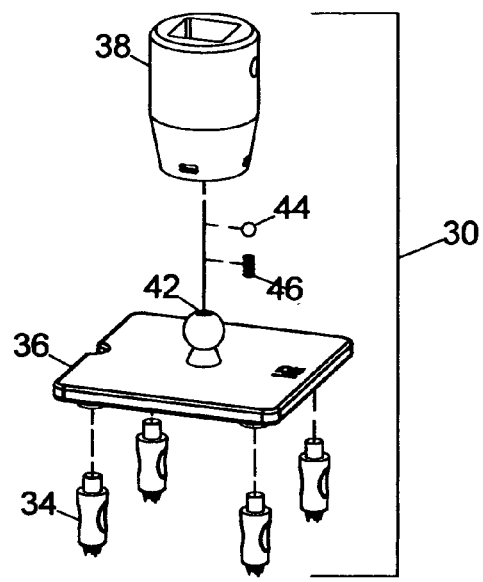
FIG. 4B show an exploded view of the testing head assembly shown in FIG. 4A.

FIG. 4A shows the testing head assembly 30, and FIG. 4B shows an exploded view of the testing head assembly 30. The testing head assembly 30 may be manufactured, for example, from titanium, machined from surgical-grade stainless steel, and the like. The testing head assembly 30 is reusable. For example, the testing head assembly 30 may be sterilized or autoclaved. The testing head assembly 30 includes a testing head 38, a baseplate 36 having a notch 32, and a socket assembly 42. Notch 32 serves to align the testing head assemblies 30 in an allergen tray (shown below in FIG. 9 and FIG. 10). The socket assembly 42 has a ball bearing 44 and a spring 46, and the socket assembly 42 disposed within the testing head 38. Further, the baseplate 36 is connected to a plurality of pins 34.

Figure 4C:
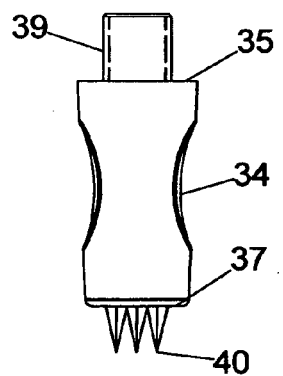
FIG. 4C shows a pin having a plurality of tips.

FIG. 4C shows a pin 34. The pin 34 has a first end 35 and a second end 37, where the first end 35 includes a male screw portion 39, and the second end 37 has a plurality of tips 40. Pin 34 has a plurality of concave indentations and, further, the surface of pin 34 is knurled for an easy grip. The male screw portion 39 screws into a female screw portion (not shown) of baseplate 36. Thus, the pin 34 is removably connected to the baseplate 36. Pin 34 is structured to be reusable, for instance, pin 34 may be sterilized or autoclaved. Further, pin 35 is structured to be independently coated with a selected allergen. The allergen may be one of a plant allergen (e.g., a tree pollen, a weed pollen, a poison ivy allergen, a poison oak allergen, a poison sumac allergen and the like), a latex allergen, an animal allergen (e.g., a dog dander allergen, a cat dander allergen, a bee sting allergen, a fish allergen and the like), an insect allergen (e.g., a cockroach allergen, a dust mite allergen and the like), a food allergen (e.g., a soy allergen, a milk allergen, an egg allergen, a wheat allergen, a shellfish allergen, a peanut allergen, a nut allergen and the like), a medicine allergen (e.g., a penicillin allergen), a mold allergen, a fungus allergen (e.g., mushroom allergen) and the like.

Figure 4D:
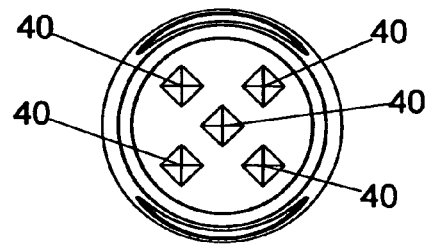
FIG. 4D shows one arrangement of the tips for the pin shown in FIG. 4C.

FIG. 4D shows one arrangement of the tips for the pin 34 shown in FIG. 4C. The plurality of tips 40 are arranged in a cross-configuration. One embodiment has at least five tips 40, but various numbers of tips may be used (e.g., three tips, six tips, nine tips and the like) depending on the layout and arrangement of the tips.

Figure 5:
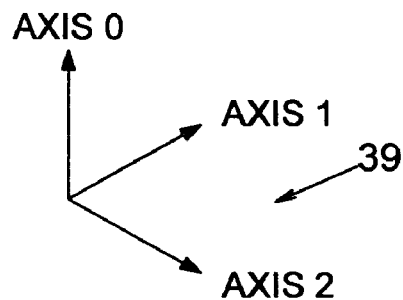
FIG. 5 shows the axes of movement of the testing head assembly shown in FIG. 4A
Figure 5:
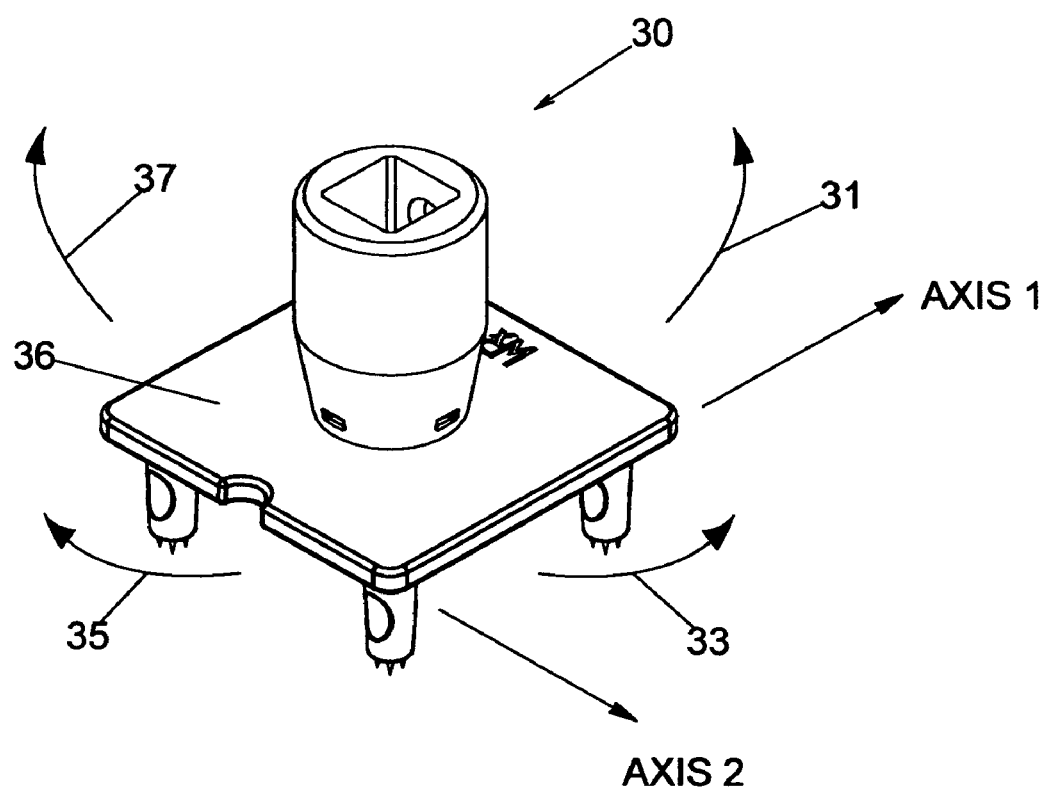

FIG. 5 shows axes of movement 39 of the testing head assembly 30. The axes of movement 39 has an axis-1 (e.g., corresponding to a z-axis), an axis-2 (e.g., corresponding to a x-axis), and an axis-0 (e.g., corresponding to a y-axis). The axes of movement 39 are in relation to the horizontal baseplate 36. Testing head assembly 30 pivots along the axis-2, as indicated by arrows 33, 37. Furthermore, testing head assembly 30 pivots along the axis-1, as indicated by arrows 31, 35. The testing head assembly 30 is structurally and operational to pivot relative to a horizontal axis in the range of about five degrees to about ten degrees. In one embodiment, the testing head assembly 30 may pivot relative to the horizontal axis in the range of about one degree to about twenty degrees.

Figure 6A:
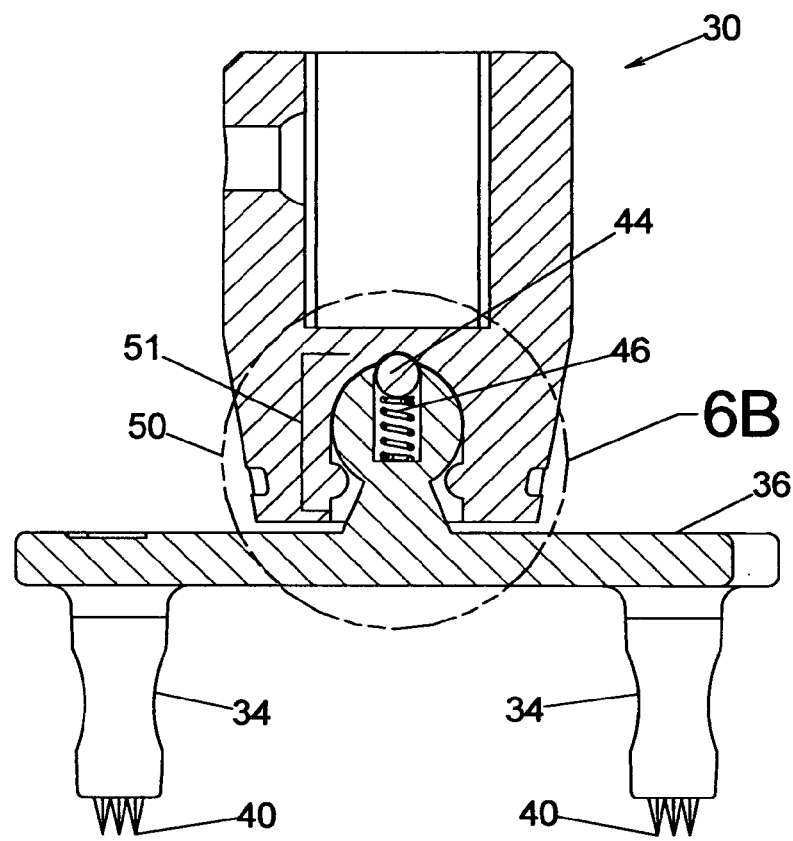
FIG. 6A shows a testing head assembly having a socket assembly.

FIG. 6A shows the testing head assembly 30 has a socket assembly 50. The socket assembly 50 has a release mechanism 51 that includes a ball bearing 44, a spring 46, and a slot 52 (shown in FIG. 6B). The slot 52 is located coaxial to a longitudinal axis of the cylinder housing 20. The ball bearing 44 is connected to the spring 46, and the ball bearing 44 is structured to rest in the slot 52 located in the testing head assembly 30.

Figure 6B:
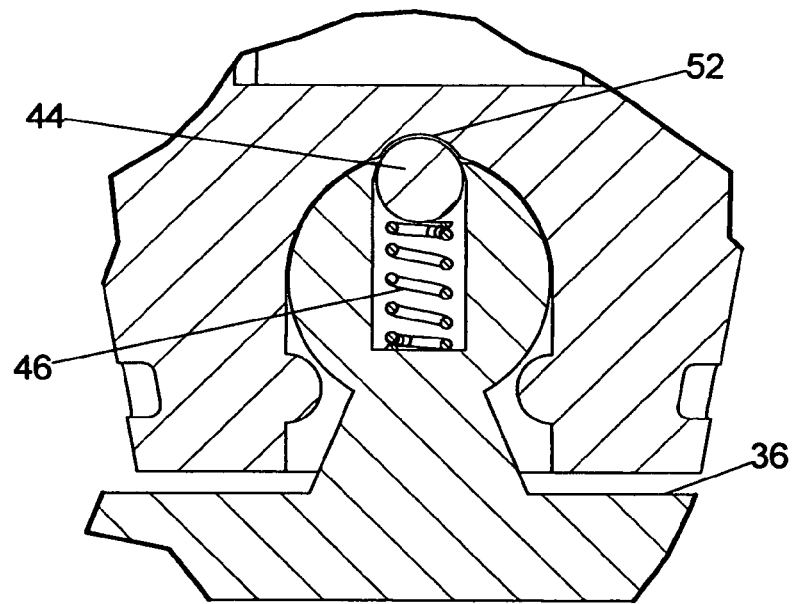
FIG. 6B shows an enlargement of the socket assembly of FIG. 6A identifying a release mechanism in a locked position.

FIG. 6B shows an enlargement of the socket assembly 50 when the release mechanism 51 is in a locked position. The release mechanism 51 is in a locked position when the ball bearing 44 is positioned in the slot 52. When in a locked position, the baseplate 36 is in a horizontal position and the testing head assembly 30 cannot pivot.

Figure 7A:
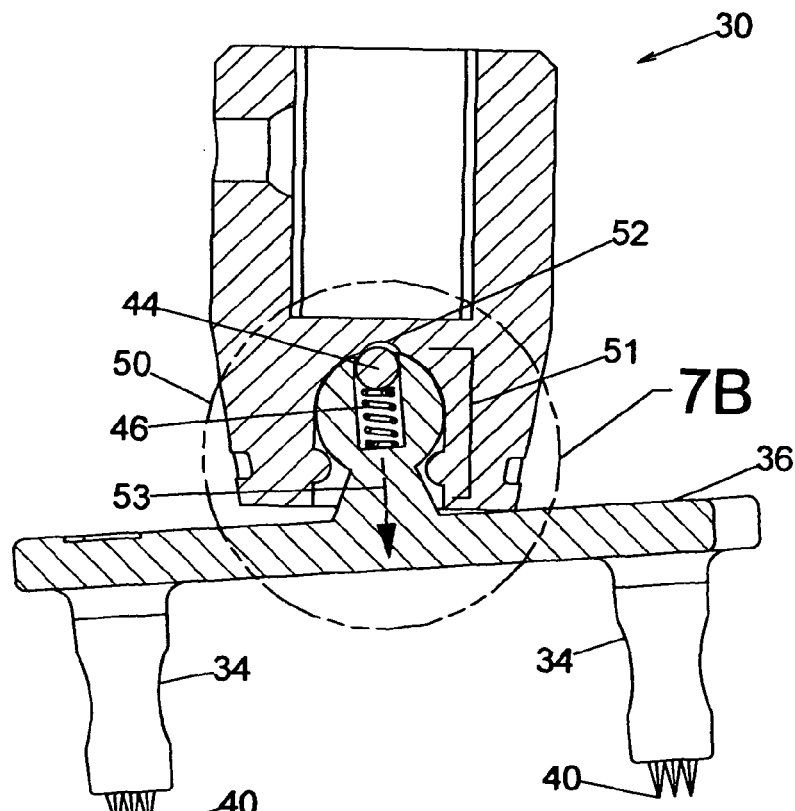
FIG. 7A shows the release mechanism of FIG. 6A in an unlocked position.
Figure 7B:
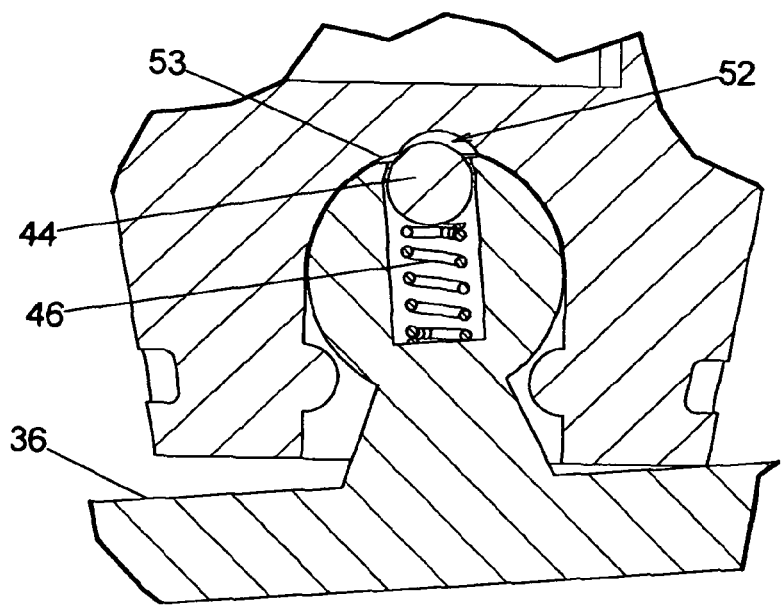
FIG. 7B shows an enlargement of the unlocked socket assembly of FIG. 7A.

FIG. 7A shows the release mechanism 51 of FIG. 6A in an unlocked position. FIG. 7B shows an enlargement of the unlocked release mechanism 51 of FIG. 7A. To unlock the release mechanism 51, the ball bearing 44 moves out of slot 52. Cylinder housing 20 (not shown) applies a pressure 53 in a longitudinal direction to the ball bearing 44 thereby compressing spring 46. The compressed spring 46 allows the ball bearing 44 to move out of slot 52, unlocking the release mechanism 51. The unlocked release mechanism 51 allows the testing head assembly 30 to pivot. Thus, the release mechanism 51 is structured and operable to be unlocked when the cylinder housing 20 applies longitudinal pressure 53 to the testing head assembly 30, resulting in the ball bearing 44 being positioned away from slot 52 allowing the testing head assembly 30 to pivot.

The unlocked release mechanism 51 permits the baseplate 36 to move out of the locked horizontal position and further allows the testing head assembly 30 to pivot from about one degree to about twenty degrees. In one embodiment, the testing head assembly 30 pivots in the range of about five degrees to about ten degrees. The ball bearing 44 connected to spring 46 acts as a positive stop for the baseplate 36, which prevents the testing head assembly 30 from pivoting beyond a predetermined range. Thus, the testing head assembly 30 is structured and operable to pivot when the ball bearing 44 depresses the spring 46. Further, the testing head assembly 30 is structured and operable to pivot based on a pressure 53 applied by the cylinder housing 20 to the testing head assembly 30, resulting in the ball bearing 44 compressing the spring 46, thereby allowing the testing head assembly 30 to pivot. The amount of pressure 53 needed to for the ball bearing 44 to compress spring 46 is minimal.

Thus, the release mechanism 51 is structured and operable in a locked position when the ball bearing 44 is positioned within the slot 52, and the release mechanism 51 is structured and operable in an unlocked position when the ball bearing 44 is positioned away from the slot 52. "Away from the slot" means that the ball bearing 44 is at least tangent to an arc 53.

Figure 8:
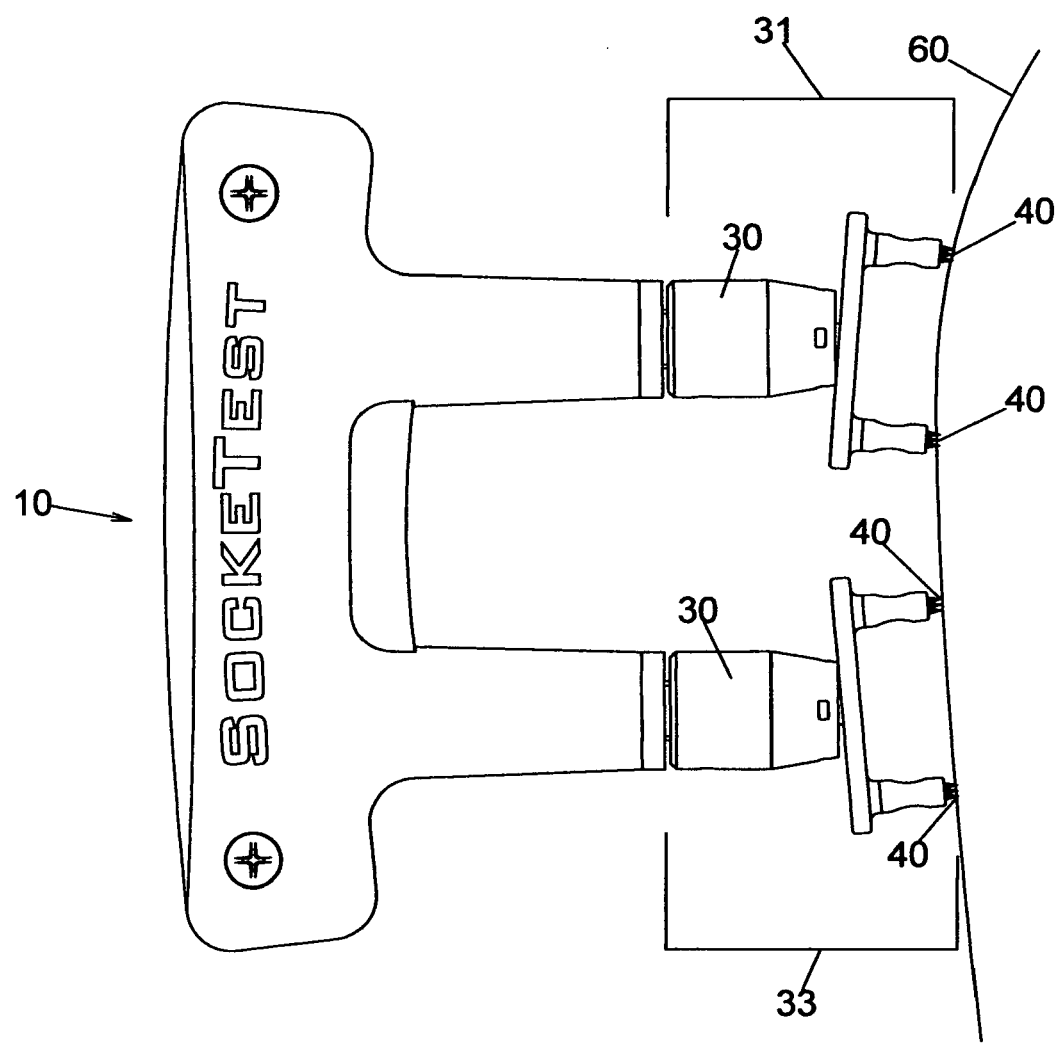
FIG. 8 shows the skin-testing device of FIG. 1 used on a back of a patient or animal.

FIG. 8 shows the skin-testing device 10 used on a back 60 of an animal or patient. As shown, the plurality of pins 40 is positionable against the skin. The back 60 is a curved structure. Therefore, when the release mechanism 51 is locked, the pressure applied to tips 40 of the testing head assembly 30 may not be equal or even. Therefore, when the tips 40 prick the surface of back 60, more pressure may be applied one set of tips 40 and less pressure may be applied to another set of tips 40. Uneven pressure applied to various sets of tips 40 may vary the amount or volume of allergen applied to the skin, which may yield a false positive result. By unlocking the release mechanism 51, the socket assembly 50 pivots the testing head assembly 30. By pivoting the testing head assembly 30, an equal and even pressure is applied to all of the tips or pins 40. The equal and even pressure applied to all the pins 40 eliminates false positive results.

Thus a method of testing patients to an allergen includes positioning the skin device 10 tangent to the surface of the skin 60, the device 10 having a handle assembly 12 connected to a cylinder assembly 20, the cylinder assembly 20 is structured and operable to attach to a plurality of testing head assemblies 30, wherein each testing head assembly includes a plurality of pins 40 structured to be coated with an allergen and to prick the surface of the skin 60, and a release mechanism 51 structured and operable to pivot the testing head assembly 30 and pivoting the testing head assembly 30 horizontally to apply equal and even pressure to the pins 40.

Figure 9A:
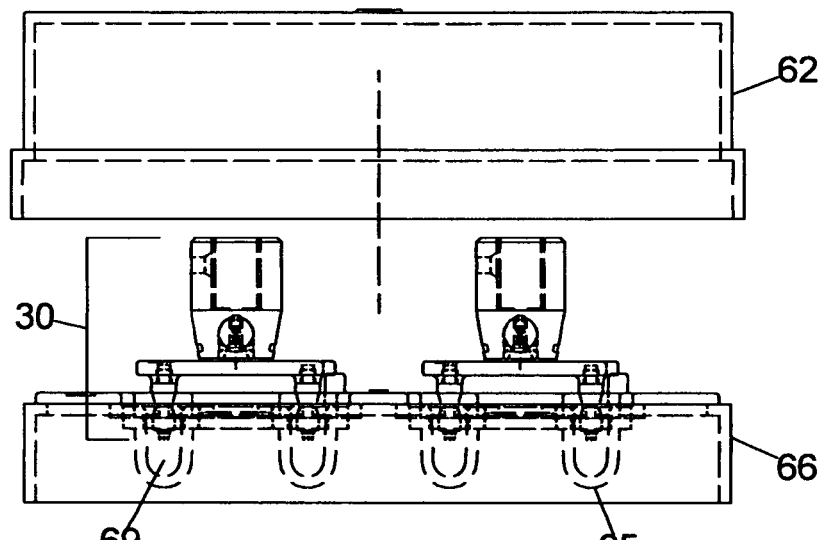
FIG. 9A shows a skin-testing kit.
Figure 9B:
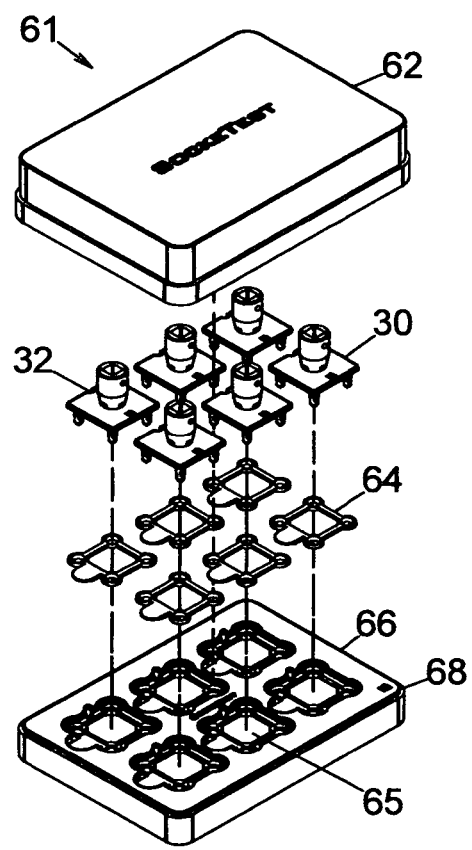
FIG. 9B shows an exploded view of the skin-testing kit.

FIG. 9A shows a skin testing kit, and FIG. 9B shows an exploded view of the skin-testing kit. The skin testing kit 61 includes a plastic cover 62, the testing head assemblies 30, a plurality of inserts 64, and a dripwell tray 66. The wells 65 of the dripwell tray 66 are filled with at least one allergen 69. Each well 65 may contain different allergens 69. The insert 64 is structured and operably fits into the dripwell tray 66 to prevent the allergen 69 from spilling out of the dripwell tray 66. The testing head assemblies 30 couple to the insert 64 allowing the pins 34 and tips 40 of the testing head assembly 30 may be coated in the allergen 69. Over a predetermined period of time, the pins 34 and tips 40 are independently coated with a selected allergen.

The plastic cover 62 may be manufactured by injection molding of an impact resistant ABS plastic or another type of plastic that is lightweight and durable. The insert 64 and the dripwell tray 66 may be manufactured by injection molding of a polycarbonate or another type of clear impact resistant plastic. The dripwell tray 66 has a lip 68 that allows multiple dripwell trays 66 to stack on top of one another.

Figure 10:
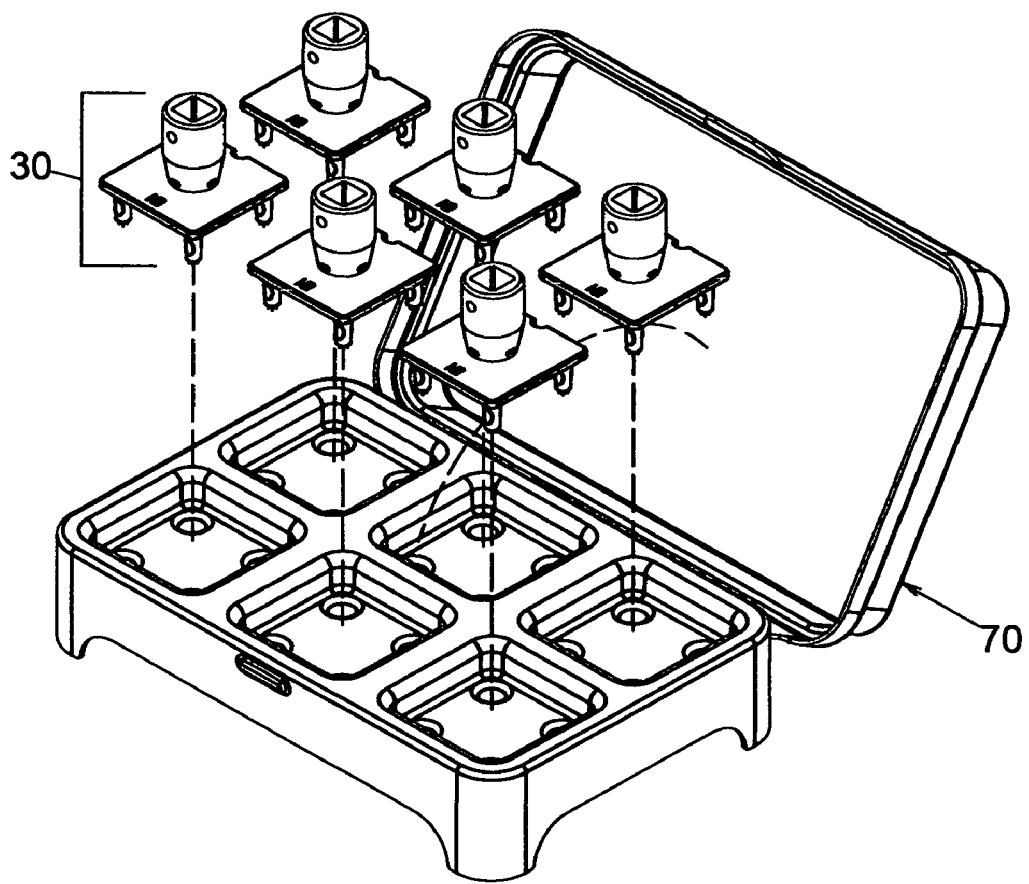
FIG. 10 shows an autoclave kit.

FIG. 10 shows an autoclave tray 70. The autoclave tray 70 may be manufactured from stainless steel metal (e.g., 18-gauge stainless steel having a thickness of at least 0.44 inches). A plurality of testing head assemblies 30 fit into the autoclave tray 70, and the autoclave tray 70 is utilized to sterilize the testing head assemblies 30 to be reused.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first,"

"second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A device for performing skin testing, comprising:
a handle assembly connected to a cylinder assembly having a first cylinder housing and a second cylinder housing, each cylinder housing connected to at least one testing head assembly, wherein the testing head assembly includes:
   a) a plurality of pins having a plurality of tips positionable against the skin;
   b) a socket assembly, wherein the socket assembly is structured and operable to pivot the testing head assembly to apply equal and even pressure to all the pins; and,
wherein the handle assembly further includes a trigger mechanism, the trigger mechanism includes a biasing device connected to a cylinder bearing shaft of the cylinder assembly that is removably connectable to the testing head assembly.

2. The device according to claim 1, wherein the cylinder bearing shaft includes a pocket structured to receive a bearing of the cylinder assembly.

3. The device according to claim 2, wherein the trigger mechanism is structured and operable to compress the biasing device such that the cylinder bearing shaft receives the bearing in the pocket thereby disconnecting the testing head assembly from the cylinder housing.

4. A device for performing skin testing, comprising:
a handle assembly connected to a cylinder assembly having a first cylinder housing and a second cylinder housing, each cylinder housing connected to at least one testing head assembly, wherein the testing head assembly includes:
   a) a plurality of pins having a plurality of tips positionable against the skin;
   b) a socket assembly, wherein the socket assembly is structured and operable to pivot the testing head assembly to apply equal and even pressure to all the pins; and,
wherein the socket assembly further includes a release mechanism having a ball bearing connected to a spring, wherein the ball bearing is structured and operable to rest in a slot located in the testing head assembly.

5. The device according to claim 4, wherein the testing head assembly is structured and operable to pivot when the ball bearing depresses the spring.

6. The device according to claim 4, wherein the slot is coaxial to a longitudinal axis of the cylinder housing.

7. The device according to claim 4, wherein the release mechanism is structured and operable in a locked position when the ball bearing is positioned within the slot, and the release mechanism is structured and operable in an unlocked position when the ball bearing is positioned away from the slot.

8. The device according to claim 4, wherein the release mechanism is structured and operable to be unlocked when the cylinder housing applies pressure to the testing head assembly resulting in the ball bearing being positioned away from the slot.

9. The device according to claim 4, wherein the testing head assembly is structured and operable to pivot based on a pressure applied by the cylinder housing to the testing head assembly, resulting in the ball bearing compressing the spring, thereby allowing the testing head assembly to pivot.

* * * * *